United States Patent [19]

Moore

[11] Plant 5,114

[45] Oct. 4, 1983

[54] ROSE PLANT

[75] Inventor: Ralph S. Moore, Visalia, Calif.

[73] Assignee: Sequoia Nursery, Visalia, Calif.

[21] Appl. No.: 342,120

[22] Filed: Jan. 25, 1982

[51] Int. Cl.[3] ..... A01H 5/00

[52] U.S. Cl. ..... Plt./10

[58] Field of Search ..... Plt./10

*Primary Examiner*—Robert E. Bagwill

[57] ABSTRACT

This invention relates to a new and distinct variety of miniature rose plant primarily identified by its bright red coloring, excellent bud form and vigorous plant habit.

1 Drawing Figure

1

The present invention relates to a new and distinct variety of hardy, dwarf, bush type rose plant of the miniature class; the variety being primarily characterized — as to novelty — by the red to orange red (almost scarlet) flowers which generally open rather flat and hold colors extremely well.

The variety is further characterized by:

An abundance of bloom, with flowers usually borne in loose spray (or cluster) but also may bloom singly.

Some fragrance.

A plant which is quite vigorous, of rounded, upright shape with small semi-glossy to matt foliage with pointed leaflets; the buds and flowers being similar in form and color to Sheri Anne (miniature — U.S. Plant Pat. No. 3,826).

The plant, which has a normal height of 16–20 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between Little Darling (U.S. Plant Pat. No. 1,581, expired — florabunda) as the seed parent and Fire Princess (miniature — U.S. Plant Pat. No. 3,084) as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded to upright; seedling; greenhouse; outdoors; cut flowers; garden decoration; potted plant.

Class: Miniature.

*Variety identification.*—MORberg (Commercial synonym: Ann Moore).

Flowers borne: Several together (3 to 5) in loose spray on slender wirey stems (sometimes singly).

2

Quantity of bloom: Abundant both outside and in greenhouse.

Bud:

*Peduncle.*—Long to medium length; slender but sturdy; erect; medium green, sometimes tinted bronze (outdoors); with no prickles and some very short fuzz-like hairs.

*Before calyx breaks.*—Size — small. Form long, pointed, with several small foliaceous apendages on surface of bud; with foliaceous parts extending beyond the tip of the bud equal to one-half or more of its length. Color — medium green, occasionally tinted with bronze (outdoors).

*As calyx breaks.*—Color — red. Opening: opens well in all weather.

Bloom:

*Size when fully open.*—Small, averaging about 45 mm ($1\frac{3}{4}''$). Petalage — double — averaging about 28–30 petals, arranged regularly plus several small petaloids. Form — cupped at first becoming more rounded, then maturing more flat with petals rolled slightly outward and downward. Open flowers have stamens.

Petals: Fairly thick; satiny on inside and on outside surface.

*Shape.*—Outside petals, broad lanceolate with nearly round tip or very short acute tip; intermediate — broad lanceolate with nearly round or short acute tip; inside — lanceolate with acute tip.

Color: Newly opened flower from a plant grown in plastic greenhouse (November 1981), Visalia, Calif.:

*Outside petal.*—Outside surface — red of a shade near Geranium Lake 20 (sometimes approaching Carmine 21) lightly overlaid or veined with darker red (near Cardinal Red 822/1); becoming white to yellowish at base. Inside surface — red — of a shade near Geranium Lake 20 (or lighter) with some darker veining but less than outside surface; small white area at base.

*Intermediate petal.*—Outside surface similar to outside petal. Inside surface similar to outside petal.

*Inner petal.*—Outside surface — similar to intermediate petal; inside surface — similar to intermediate petal. General color effect; buds and newly opened flowers — bright lively red — near scarlet red. Three days open — color — similar to fresh open flowers. Behavior — opens well in all weather. Spent petals or flowers drop off. Flower longevity (September 1981) — plant in pot 7–10 days or longer. Cut flowers at living room temperature 5–7 days or longer.

Reproductive organs:

*Stamens.*—Fairly abundant.

*Filaments.*—Varying length.

*Anthers.*—Yellow.

*Pollen.*—Quite abundant.

*Pistils.*—Average number.

*Styles.*—Varying length; near white; bunched.

*Ovaries.*—All enclosed in calyx.

*Hips.*—Some.

*Sepals.*—Permanent; spear shaped; recurved.

*Seed.*—Some.

Foliage:

*Leaves.*—Compound of five (sometimes three or seven) leaflets; medium small; leathery; semi-glossy to matt.

*Leaflets.*—Shape: broad, lanceolate; apex acute; base — acute — sometimes rounded. Color: medium green; new growth — normal (medium) green, usually tinted reddish. Rachis: medium strength; upper side may have a few very short hairs and/or tiny prickles; grooved; underside may have 2 or 3 small thorns (or claws) and few or no tiny short prickles. Stipules: medium length; medium width; short length narrow points which turn out usually at about 45 degrees or more.

Growth:

*Habit.*—Dwarf; bushy; rounded to upright; much branched.

*Growth.*—Vigorous; internodes moderately short.

*Canes.*—Medium; slender; sturdy.

*Main stems.*—Color: medium green.

*Thorns.*—Several — slender; medium length; brown. Nearly straight, inclined downward. Hairs — generally none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded to upright, much branched habit, substantially as illustrated and described, characterized by buds and flowers which resemble Sheri Anne (miniature — U.S. Plant Pat. No. 3,826) in form and color, the flowers of the present variety being born usually in loose sprays on relatively long stems (sometimes born singly) suitable for cutting, the flowers retaining good color and quality for several days as cut flowers; and further characterized by a vigorous healthy plant with semi-glossy to matt foliage, the plant being easy to propagate from softwood cuttings and by budding.

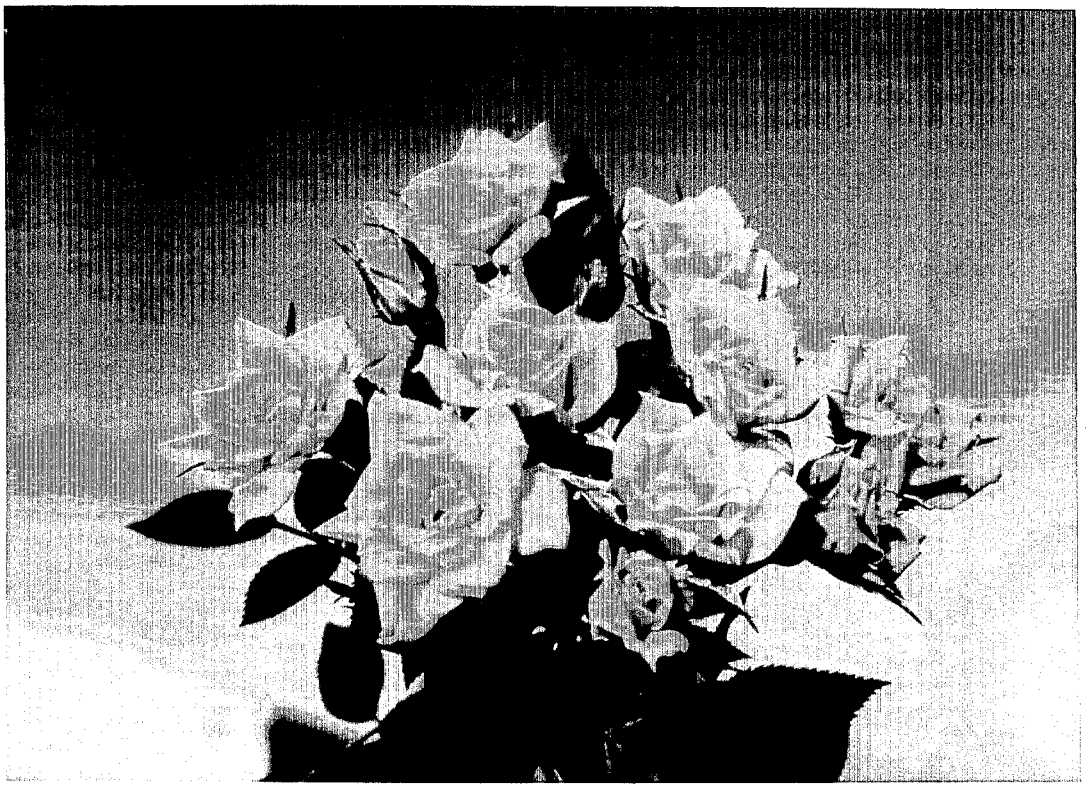

* * * * *